US011208471B2

(12) United States Patent
Barnett et al.

(10) Patent No.: US 11,208,471 B2
(45) Date of Patent: *Dec. 28, 2021

(54) METHOD FOR TREATING INFECTIOUS DISEASES USING A COMPOSITION COMPRISING PLASMA-DERIVED IMMUNOGLOBULIN M (IGM)

(71) Applicant: Grifols Worldwide Operations Limited, Dublin (IE)

(72) Inventors: Thomas Barnett, Chapel Hill, NC (US); David A. Ross, Cary, NC (US)

(73) Assignee: Grifols Worldwide Operations Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/745,563

(22) Filed: Jan. 17, 2020

(65) Prior Publication Data

US 2020/0223908 A1  Jul. 16, 2020

Related U.S. Application Data

(63) Continuation of application No. 15/156,562, filed on May 17, 2016, now Pat. No. 10,570,194.

(60) Provisional application No. 62/201,910, filed on Aug. 6, 2015.

(51) Int. Cl.
| A61K 39/40 | (2006.01) |
| C07K 16/12 | (2006.01) |
| A61K 31/407 | (2006.01) |
| A61K 38/14 | (2006.01) |
| A61K 38/17 | (2006.01) |
| A61K 39/00 | (2006.01) |

(52) U.S. Cl.
CPC ........ *C07K 16/1282* (2013.01); *A61K 31/407* (2013.01); *A61K 38/14* (2013.01); *A61K 38/1741* (2013.01); *A61K 39/40* (2013.01); *C07K 16/12* (2013.01); *C07K 16/1214* (2013.01); *C07K 16/1232* (2013.01); *C07K 16/1271* (2013.01); *A61K 2039/545* (2013.01); *C07K 2317/52* (2013.01); *C07K 2317/76* (2013.01)

(58) Field of Classification Search
None
See application file for complete search history.

(56) References Cited

U.S. PATENT DOCUMENTS

| 4,918,163 | A | 4/1990 | Young |
| 5,240,909 | A | 8/1993 | Nitsche |
| 5,410,025 | A | 4/1995 | Moller et al. |
| 6,307,028 | B1 | 10/2001 | Lebing et al. |
| 7,794,721 | B2 | 9/2010 | Simon |
| 9,913,903 | B2 * | 3/2018 | Barnett ............... C07K 16/1228 |
| 10,570,194 | B2 * | 2/2020 | Barnett ............... A61K 39/40 |
| 10,660,956 | B2 * | 5/2020 | Barnett ............... A61P 43/00 |
| 2003/0185827 | A1 | 10/2003 | Rodriguez et al. |
| 2008/0145370 | A1 | 6/2008 | Simon |
| 2008/0260822 | A1 | 10/2008 | Simon et al. |
| 2008/0317857 | A1 | 12/2008 | Farina et al. |
| 2010/0297187 | A1 | 11/2010 | Stoloff et al. |
| 2011/0059085 | A1 * | 3/2011 | Kim ............... C07K 16/1271 424/133.1 |
| 2018/0153991 | A1 | 6/2018 | Barnett et al. |

FOREIGN PATENT DOCUMENTS

| CL | 2016001977 A1 | 3/2017 |
| EP | 303088 A2 | 2/1989 |
| EP | 0345543 A2 | 12/1989 |
| EP | 3150629 A2 | 4/2017 |
| JP | 61-204200 A | 9/1986 |
| JP | 3-204822 A | 9/1991 |
| WO | 8602362 A1 | 4/1986 |
| WO | 2009140236 A2 | 11/2009 |
| WO | 2010/037402 A1 | 4/2010 |
| WO | 2014/074503 A1 | 5/2014 |

OTHER PUBLICATIONS

Japanese Office Action dated Nov. 18, 2019 in Japanese Patent Application No. 2016-146098, 11 pages.
Neter, "Bacterial Hemagglutination and Hemolysis", Bacteriology Reviews, 1956, vol. 20, No. 3, pp. 166-188.
Argentinean Office Action dated Feb. 13, 2020 in Argentinean Patent Application No. 20160102381, 3 pages.
Marcuzzi et al., "Effects of antl-IgM suppression on polyclonally activated murine B cells: analysis of Immunoglobulin mRNA, gene specific nuclear factors and cell cycle distribution", Nucleic Acids Research, (Jan. 1, 1989), vol. 17, No. 24, doi:10.1093/nar/17.24. 10455, ISSN 0305-1048, pp. 10455-10472.
Russian Office Action dated Apr. 2, 2020 in Russian Patent Application No. 2016131195/04(048456), 13 pages.
Bhimani et al., "Influence of lactoferrin feeding and injection against systemic staphylococcal infections in mice", Journal of Applied Microbiology, Jan. 1999, vol. 86, pp. 135-144.
Breen et al., "High-throughput fractionation of human plasma for fast enrichment of low- and high-abundance proteins", Blood Transfus., May 2012, 12 pages.
Taiwanese Office Action dated May 11, 2020 in Taiwanese Patent Application No. 105124305, 22 pages.
Tugrul et al., "The effects of IgM enriched immunoglobulin preparations in patients with severe sepsis", Critical Care, Aug. 2002, vol. 6, No. 4, pp. 357-362.
Ourth, "Neutralization of bacterial exotoxin (tetanus toxin) by channel catfish IgM antibody", Immunology, 1982, vol. 45, No. 49, pp. 49-53.

(Continued)

*Primary Examiner* — Mary Maille Lyons
(74) *Attorney, Agent, or Firm* — Dinsmore & Shohl LLP

(57) ABSTRACT

Compositions and methods of the present invention prevent, inhibit or reduce the toxic effects of proteins and toxins secreted from microbes. A method for neutralizing microbial protein products in a subject comprises administering a composition to the subject, said composition comprising plasma-derived IgM and optionally one or more excipients in a pharmaceutical carrier, wherein the composition is administered in an amount effective to neutralize the microbial protein products.

13 Claims, 8 Drawing Sheets

(56) References Cited

OTHER PUBLICATIONS

Barratt-Due et al., Polyvalent Immunoglobulin Significantly Attenuated the Formation of IL-1 (beta) in *Escherichia coli*-Induced Sepsis in Pigs, Immunobiology, 2012, pp. 683-689, vol. 218, No. 5.

Cesena, et al., Immune-modulation by polycylonal IgM treatment reduces atherosclerosis in hypercholesterolemic apoE-/-mice, Atherosclerosis, 220, pp. 59-65, 2012.

Hurez, et al., Pooled Normal Human Polyspecific IgM Contains Neutralizing Anti-Idiotypes to IgG Autoantibodies of Autoimmune Patents and Protects from Experimental Autoimmune Disease, Blood, vol. 90, No. 10, 1997, pp. 4004-4013.

Kreymann et al., Use of polyclonal immunoglobulins as adjunctive therapy for sepsis or septic shock, Critical Care Medicine, 2007, vol. 35, No. 12, pp. 2677-2685.

Linevsky et al., IL-8 release and neutrophil activation by Clostridium difficile toxin-exposed human monocytes, Am. J. Physiol. Gastrointest. Liver Physiol., 273: G1333-G1340, 1997.

Massironi et al., Minimal Concentation of Human IgM and IgG Antibodies Necessary to Protect Mice from Challenges with Live O6 *Escherichia coli*, FEMS Immunology and Medical Microbiology, 2011, pp. 193-201, vol. 63, No. 2.

Oesser et al., Protective capacity of a IgM/IgA-enriched polyclonal immunoglobulin-G preparation in endotoxemia, Res. Exp. Med., vol. 198, pp. 325-339, 1999.

Rossmann et al., In Vitro and In Vivo Activity of Hyperimmune Globulin Preparations Against Multiresistant Nosocomial Pathogens, Infection, 2014, pp. 169-175, vol. 43, No. 2.

Sun et al., Essential role of the glucosyltransferase activity in Clostridium difficile toxin-induced secretion of TNF-a by macrophages, Microbial Pathogenesis, 16:298-305, 2009.

Tatum, Large scale recovery of biologically active IgM (95% pure) from human plasma obtained by therapeutic plasmapheresis, Journal of Immunological Methods, vol. 158, pp. 1-4, 1993.

Tramont et al., Progress in the development of an HIV vaccine, Expert Opinion on Emerging Drugs, vol. 8, No. 1, pp. 37-45, 2003.

Wand et al., IgM-Enriched Immunoglobulin Attenuates Systemic Endotoxin Activity in early Severe Sepsis: A Before-After Cohort Study, Plos One, 2016, pp. 1-13, vol. 11, No. 8.

Norby-Teglund et al., Intravenous Polyclonal IgM-Enriched Immunoglobulin Therapy in Sepsis: A Review of Clinical Efficacy in Relation to Microbiological Aetiology and Severity of Sepsis, Journal of Internal Medicine, 2006, pp. 509-516; vol. 260, No. 6.

Mahassni et al., Purification of a Murine IgM Monoclonal Antibody, Hybridoma, vol. 28, No. 3, 2009, pp. 189-197.

Gagnon et al., Purification of IgM Monoclonal Antibodies, BioPharma, 2008, pp. 1-10.

Extended European Search Report, dated Mar. 17, 2017, in European Patent Application No. 16179975.4, 11 pages.

Chilean Office Action, dated Jan. 17, 2018, in corresponding Chilean Patent Application No. 2016-0176.

Kamran Mousavi Hosseine, et al., Preparation of Enriched Immunoglobulin M and Immunoglobulin A from Human Plasma, Medical Journal of Islamic Republic of Iran, vol. 17, No. 4, Winter 1382, Feb. 2004, pp. 315-318.

Sharad P. Adekar et al;, A Natural Human IgM Antibody that Neutralizes Botulinum Neurotoxin in vivo, Hybridoma, vol. 27, No. 2, Apr. 1, 2008, pp. 65-69.

European Patent Office Search Report dated Jan. 13, 2017 in reference to co-pending European Patent Application No. 16180425.7.

Nair et al., "Impact of *Staphylococcus aureus* on Pathogenesis in Polymicrobial Infections"; Infection and Immunity 82(6): 2162-2169, 2014.

Adekar et al., "A Natural Human IgM Antibody that Neutralizes Botulinum Neurotoxin in vivo," Hybridoma 27(2): 65-69, 2008.

Norrby-Teglund et al., "Relative Neutralizing Activity in Polyspecific IgM, IgA, and IgG preparations against Group A Streptococcal Superantigens," Clinical Infectious Diseases 31: 1175-1182, Year: 2000.

\* cited by examiner

FIGURES

METHOD FOR TREATING INFECTIOUS DISEASES USING A COMPOSITION COMPRISING PLASMA-DERIVED IMMUNOGLOBULIN M (IGM)

CROSS REFERENCE TO RELATED APPLICATIONS

This application is a continuation of U.S. patent application Ser. No. 15/156,562, filed May 17, 2016, which claims priority to U.S. Provisional Patent Application No. 62/201,910, filed Aug. 6, 2015, the contents of all of which are specifically incorporated herein by reference.

FIELD OF THE INVENTION

The present invention relates to a method for treating infectious diseases comprising the administration to a patient in need thereof of a composition containing plasma-derived IgM. The present invention also relates to a method for neutralizing secreted cytotoxic exotoxins during active microbial infections comprising the administration to a patient in need thereof of a composition containing plasma-derived IgM.

BACKGROUND OF THE INVENTION

Microbial species can become highly deleterious to an infected patient, if that individual cannot clear the infection, or if the patient is unresponsive to treatment. Infections can also become septic, spreading from an infected organ into the blood stream. These septic infections have a poor outcome for patients, generally resulting in organ failure and death.

The problem is that most antibiotics target the live microbes themselves to treat the infection. IgM has been characterized as preventing the toxic septic aspects of bacterial infections due to systemic effects of microbial endotoxins. These endotoxins are components of the cell wall (in-particular in Gram-negative bacteria). Neither of these methods of treatment target or have been shown to target microbial exotoxins, superantigens, or secreted enzymes.

While it is well characterized that plasma-derived IgM can bind to and prevent endotoxin-mediated toxicity towards a patient, this does not address other proteins and toxins that are actively secreted from microbes. The toxic effects of endotoxins are typically a response to bacterial death or lysis induced by antibiotics or the immune system of the patient. These effects are separate from the toxic events that are observed during a microbial infection due to proteins, such as exotoxins, that are actively secreted by the microbe. There remains a need for compositions and methods that prevent, inhibit or reduce the toxic effects of proteins and toxins secreted from microbes, other than endotoxins.

SUMMARY OF THE INVENTION

The present invention is based on the findings of a surprising neutralization effect of therapeutic doses of plasma-derived IgM to neutralize the deleterious impact of the secreted microbial proteins, such as secreted cytotoxic exotoxins, during active microbial infections. The present invention makes use of the specificity of plasma-derived IgM towards microbial proteins. As explained above, it is well known that IgM binds microbial endotoxins, which are glycoproteins, and that this binding makes use of the general binding of IgM towards glycoproteins and carbohydrates.

In the prior art, several monoclonal antibodies have been described, but are individually directed only to a single antigenic target. Natural plasma-derived IgM, on the other hand, contains a plethora of potential antigen binding sites that can target may different antigens simultaneously and thus do not rely on a single treatment modality.

Furthermore, the present invention makes use of a source of IgM derived from a waste stream of a standard blood fractionation process, for example Grifols' Gamunex fractionation process.

Therefore, in a first aspect, the present invention refers to a method for treating infectious diseases comprising the administration to a patient in need thereof of a composition containing plasma-derived IgM. Stated another way, an embodiment of the present invention provides a method for treating an infectious disease in a subject, said method comprising administering a composition to said subject, said composition comprising, consisting essentially of, or consisting of plasma-derived IgM and optionally one or more excipients in a pharmaceutical carrier, wherein the composition is administered in an amount effective to neutralize microbial protein products in said patient.

In a second aspect, the present invention refers to a method for neutralizing secreted cytotoxic exotoxins during active microbial infections comprising the administration to a patient in need thereof of a composition containing plasma-derived IgM. Stated another way, an embodiment of the present invention provides a method for neutralizing microbial protein products in a subject, said method comprising administering a composition to said subject, said composition comprising, consisting essentially of, or consisting of plasma-derived IgM and optionally one or more excipients in a pharmaceutical carrier, wherein the composition is administered in an amount effective to neutralize said microbial protein products.

Said cytotoxic exotoxins can be secreted by several microorganisms such as *Escherichia coli, Pseudomonas aeruginosa, Staphyloccuc aureus, Klebsiella pneumoniae, Streptococcus pneumoniae, Clostridium difficile, Clostridium botulinum, Aspergillus flavus* and combinations thereof.

Preferably, the composition containing plasma-derived IgM is obtained from a waste stream of a standard fractionation process. The plasma-derived IgM has a purity of at least 70% (w/v), more preferably at least 90% (w/v), and the most preferably at least 95% (w/v).

Also preferably, the dose of plasma-derived IgM to be administered ranges from 75 mg to 1 g per kilogram of the patient, preferably from 75 mg/kg to 600 mg/kg, more preferably from 75 mg/kg to 300 mg/kg. The dose can be administered on a daily, every other day, 3×/week or once per week, regimen.

Optionally, the composition of plasma-derived IgM further comprises other molecules selected from small molecule antibiotics, natural or synthetic peptide antimicrobials, or proteins with antimicrobial properties, or a combination thereof.

Examples of small molecule antibiotics are vancomycin and meropenem. An example of proteins with antimicrobial properties is lactoferrin.

In the method of the present invention, the composition of plasma-derived IgM can be used alone or in combination with other therapeutics molecules selected from the group consisting of therapeutic molecules, including anti-inflammatory agents, and immunomodulators.

BRIEF DESCRIPTION OF THE DRAWINGS

Embodiments of the present invention will be described below in reference to the following figures in which:

FIG. 2A demonstrates specificity of neutralization of *C. difficile* Toxin B (Tox B) by a two different batches of an IgG and IgM mixture (Frac. Conc. 45% and 70-80% IgM for solid black bars and hatched bars, respectively, but not for the non-specific control, human serum albumin (open bar); FIG. 2B further demonstrates neutralization of *C. difficile* Toxin B (ToxB) and rescue of viability of cells by increasing concentrations of virtually pure IgM only (in micromole/L or uM; solid black bar).

FIG. 4A demonstrates specificity of neutralization of *Pseudomonas* Exotoxin A (ExA) by a two different batches of an IgG and IgM mixture (Frac Conc. 45% and 70-80% IgM for solid black bars and hatched bars, respectively, but not for the non-specific control, human serum albumin (open bar); FIG. 4B further demonstrates neutralization of *Pseudomonas* Exotoxin A (P.A. ExA) and rescue of viability of cells by increasing concentrations of virtually pure IgM only (in micromole/L or uM; solid black bars).

DETAILED DESCRIPTION OF THE INVENTION

Figure 1:
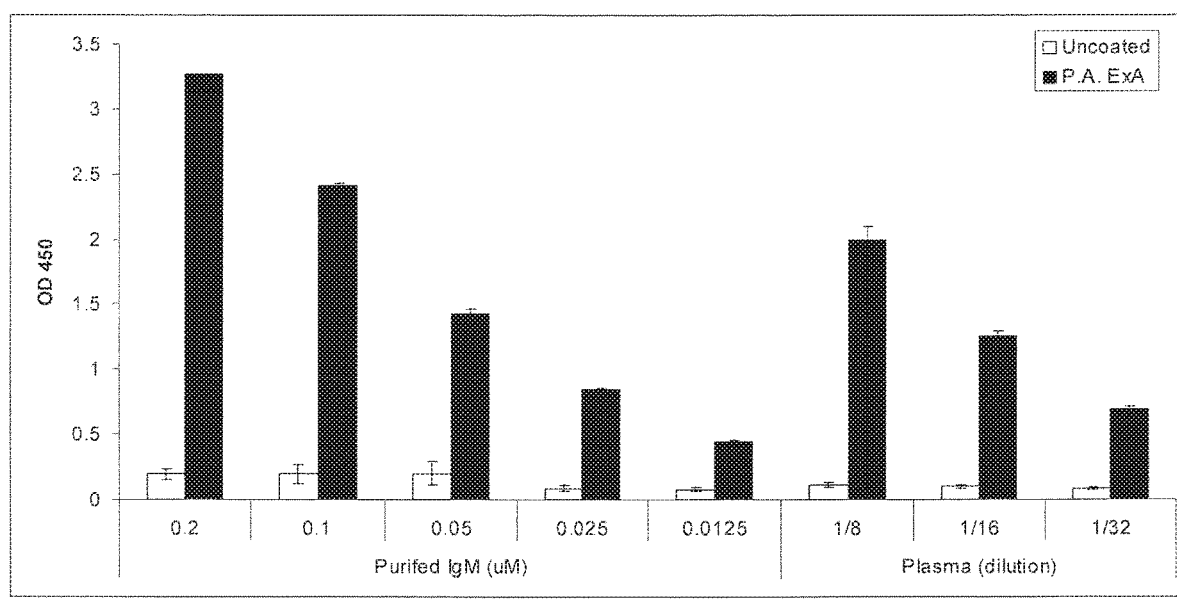
FIG. 1 shows the immunoreactivity of IgM against *P. aeruginosa* Exotoxin A. Absorbance OD readings at 450 nm are shown for a representative ELISA. The target antigen, *P. aeruginosa* Exotoxin A (P.A. ExA), was coated on ELISA plates. Pooled plasma or IgM purified from the Gammunex process was used as sources of IgM. Various dilutions of this sample were tested, as indicated, in PBS. Controls are wells that have not been coated with antigen (Uncoated). Standard deviations are shown for each bar.

An embodiment of the present invention provides a method for treating an infectious disease in a subject, said method comprising administering a composition to said subject, said composition comprising, consisting essentially of, or consisting of plasma-derived IgM and optionally one or more excipients in a pharmaceutical carrier, wherein the composition is administered in an amount effective to neutralize microbial protein products in said patient.

Another embodiment of the present invention provides a method for neutralizing microbial protein products in a subject, said method comprising administering a composition to said subject, said composition comprising, consisting essentially of, or consisting of plasma-derived IgM and optionally one or more excipients in a pharmaceutical carrier, wherein the composition is administered in an amount effective to neutralize said microbial protein products.

Another embodiment of the present invention provides a composition comprising, consisting essentially of, or consisting of plasma-derived IgM and optionally one or more excipients in a pharmaceutical carrier. According to particular embodiments, the one or more excipients and/or the pharmaceutical carrier are synthetic, i.e., non-naturally occurring.

As used herein, "neutralizing" microbial protein products refers to reducing, preventing or eliminating the toxic effects of microbial protein products on the subject, e.g., reducing, preventing or eliminating exotoxin-mediated toxicity towards a patient.

According to particular embodiments, the microbial protein products are selected from the group consisting of exotoxins, superantigens and secreted enzymes. Preferably, the microbial protein products do not include microbial endotoxins.

According to particular embodiments, the subject has been diagnosed with a bacterial infection prior to administration of the composition.

As used herein, the term "pharmaceutically acceptable carrier" refers to a diluent, adjuvant, excipient, or vehicle with which plasma-derived IgM of the present invention is administered. Such carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Saline solutions and aqueous dextrose and glycerol solutions can also be employed as liquid carriers, particularly for injectable solutions. According to particular embodiments, the pharmaceutically acceptable carrier is synthetic (i.e., the carrier is not naturally-occurring).

Non-limiting examples of suitable excipients include starch, glucose, lactose, sucrose, gelatin, silica gel, sodium stearate, glycerol monostearate, talc, sodium chloride, glycerol, propylene glycol, water, ethanol and the like. Excipients may also include wetting or emulsifying agents, or pH buffering agents such as acetates, citrates or phosphates; antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose. According to particular embodiments, the one or more excipients are synthetic (i.e., the excipients are not naturally-occurring).

The cytotoxic exotoxins can be secreted by several microorganisms such as *Escherichia coli, Pseudomonas aeruginosa, Staphyloccuc aureus, Klebsiella pneumoniae, Streptococcus pneumoniae, Clostridium difficile, Clostridium botulinum, Aspergillus flavus* and combinations thereof.

Preferably, the composition containing plasma-derived IgM is obtained from a waste stream of a standard fractionation process. The plasma-derived IgM has a purity of at least 70% (w/v), more preferably at least 90% (w/v), and the most preferably at least 95% (w/v).

Also preferably, the dose of plasma-derived IgM to be administered ranges from 75 mg to 1 g per kilogram of the patient, preferably from 75 mg/kg to 600 mg/kg, more preferably from 75 mg/kg to 300 mg/kg. The dose can be administered on a daily, every other day, 3×/week or once per week, regimen.

Optionally, the composition of plasma-derived IgM further comprises other molecules such as small molecule antibiotics, natural or synthetic peptide antimicrobials, or proteins with antimicrobial properties, or a combination thereof.

Examples of small molecule antibiotics are vancomycin and meropenem. An example of proteins with antimicrobial properties is lactoferrin.

In the method of the present invention, the composition of plasma-derived IgM can be used alone or in combination with other therapeutics molecules selected from the group consisting of therapeutic molecules, including anti-inflammatory agents, and immunomodulators.

The embodiments described herein are intended to be exemplary of the invention and not limitations thereof. One skilled in the art will appreciate that modifications to the embodiments and examples of the present disclosure may be made without departing from the scope of the present disclosure.

The embodiments of the invention are described above using the term "comprising" and variations thereof. However, it is the intent of the inventors that the term "comprising" may be substituted in any of the embodiments described herein with "consisting of" and "consisting essentially of" without departing from the scope of the invention. Unless specified otherwise, all values provided herein include up to and including the starting points and end points given.

The following examples further illustrate embodiments of the invention and are to be construed as illustrative and not in limitation thereof.

EXAMPLES

Example 1. Immunoreactivity of IgM with Exotoxins, Secreted Bacterial Enzymes and Superantigens Several ELISAs were developed by the present inventors to assess immunoreactivity towards a variety target antigens produced by the bacteria *P. aeruginosa, Staphilococcus aureus, C. tetani*, and *C. difficile* (see Table 1). Surprisingly, all proteinacious exotoxins and enzymes were recognized by plasma-derived IgM. A positive reactivity for all protein-based antigens assessed from these pathogens was observed. An example ELISA showing reactivity of IgM in a purified preparation and in plasma is shown in FIG. 1.

TABLE 1

Summary of antigenic targets that have been assessed by ELISA. The symbol "+" indicates positive reactivity. *E. coli* LPS was used as a positive control, as it is well characterized that IgM has reactivity against Gram-negative endotoxins.

| Species/Antigen | IgM Reactivity |
| --- | --- |
| *P. aeruginosa* Exotoxin A | + |
| *S. aureus* TSST-1 | + |
| *S. aureus* Staphylokinase | + |
| *C. difficile* Toxoid A | + |
| *C. difficile* Toxoid B | + |
| *C. difficile* Toxin A | + |
| *C. difficile* Toxin B | + |
| *C. tetani* Tetanus Toxoid | + |
| *E. coli* 0111:B4 LPS | + |

Example 2. Neutralization of Cytotoxic Effects of *C. difficile* Toxin B

A preliminary goal of the present invention was to provide proof-of-concept for IgM neutralizing exotoxins. Since *C.*

Figure 2A:
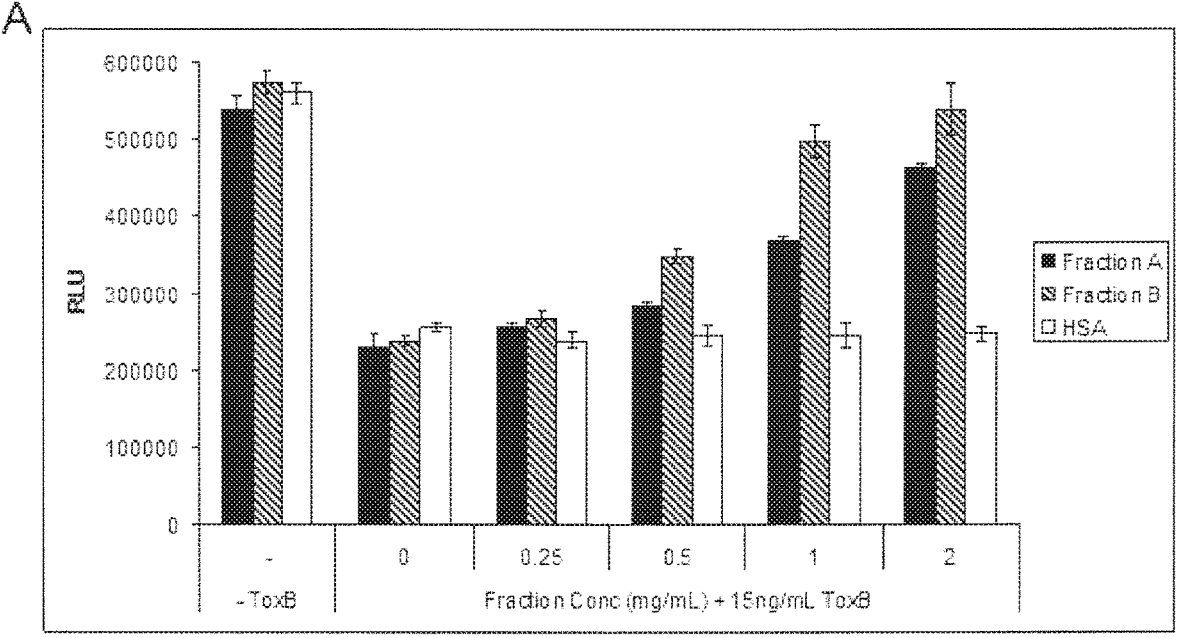
FIGS. 2A and 2B show the neutralization of *C. difficile* Toxin B cytotoxicity. Caco-2 cells (obtained from ATCC) were cultured in the recommended proliferation media. Cells were seeded in 96-well plates at 8000 cells per well. 24 hours after initial plating, cells were treated with various IgM preparations and/or *Clostridium difficile* Toxin B as described in the figure legend. Data for the relative number of cells are shown as RLU, as measured by the Cell Titer Glow (Promega Corp. Madison, Wis., USA) assay performed according to the manufacturer's instructions.
Figure 2B:
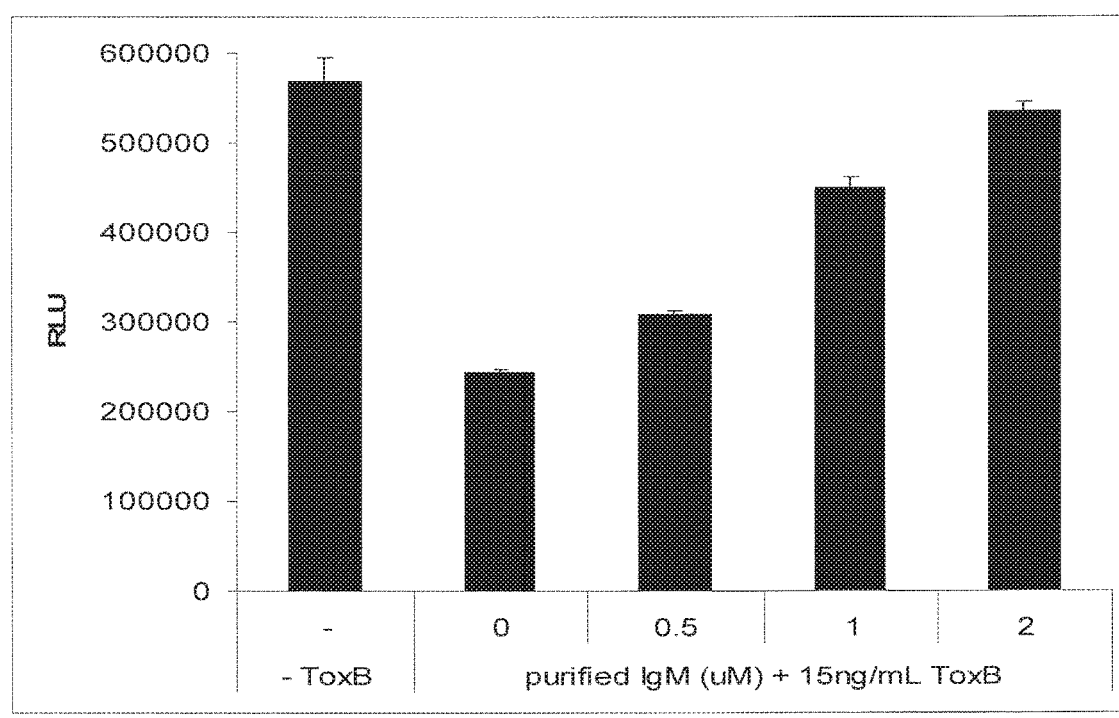

*difficile* is an intestinal infection, it was chosen to utilize a physiologically relevant cell line for studies. Caco-2 cells are an epithelial colorectal cell line routinely used for intestinal permeability studies. Caco-2 to be used in cytotoxicity assays was developed. Incubation time and *C. difficile* Toxin B concentrations were optimized (data not shown). Incubation of Toxin B for 24 hours did not show any toxicity and as incubation time increased the cytotoxicity also increased. Additionally, we determined that 25 ng/mL gave the highest assay window of toxicity at 48 hours and showed a plateau at this point. Concluding assay conditions were set at 15 ng/mL Toxin B with 48 hours incubation with proliferating cells. Using these conditions neutralization of toxin with purification fractions enriched for IgM was assessed and compared, as well as purified IgM (FIG. 2). Fraction A contains 40-50% IgM and Fraction B contains 70-80% IgM. HSA had no effect on Toxin B toxicity, whereas 2 different fractions containing IgM neutralized the toxin (FIG. 2A). Purified IgM (≥95% IgM) was also shown to be efficacious in neutralizing *C. difficile* Toxin B (FIG. 2B). There are clearly neutralizing antibodies toward *C. difficile* in Fraction A, Fraction B, and purified IgM.

Example 3. Neutralization of *C. difficile* Toxin B-Induced Permeability

Figure 3:
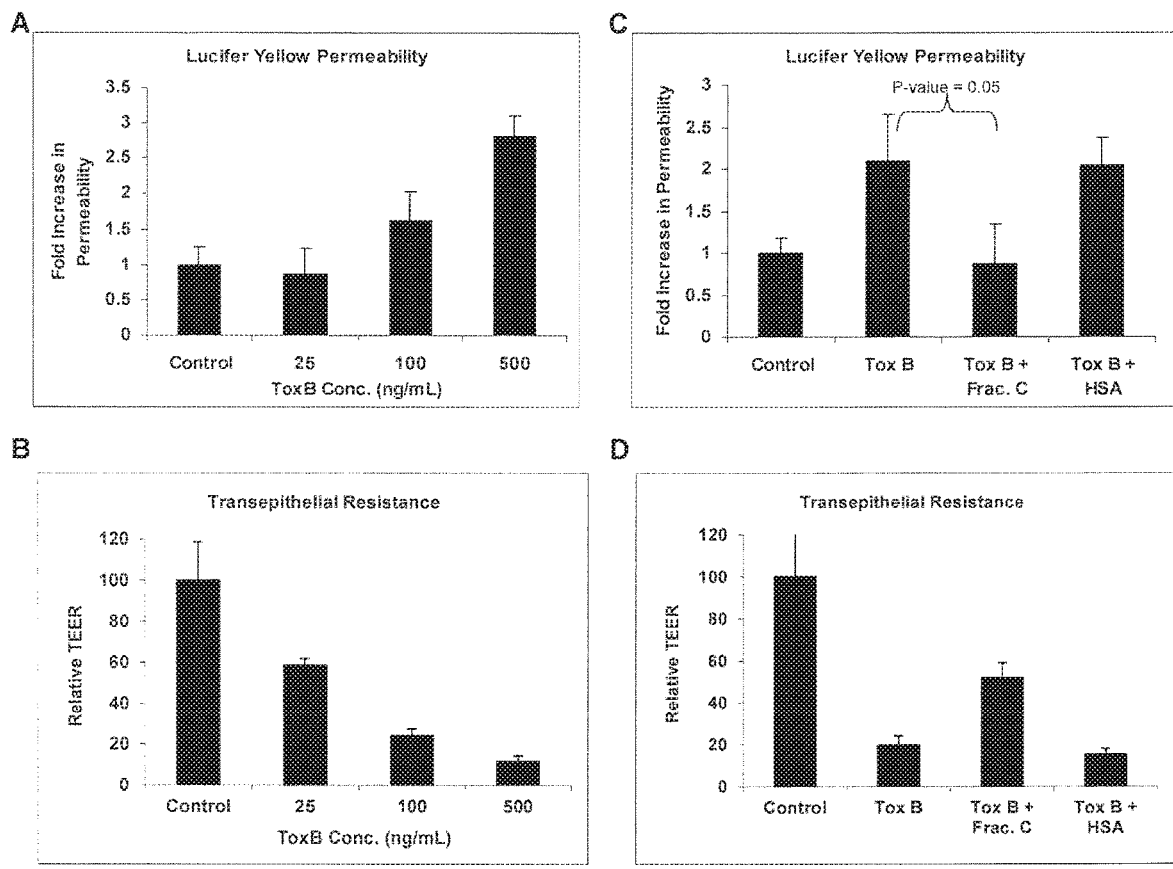
FIG. 3 shows the neutralization of *C. difficile* toxin-induced Caco-2 permeability. Caco-2 cells were differentiated by typical methods in Transwell multiwell plate inserts. After 21 days of differentiation, Transepithelial electrical resistance (TEER) was measured immediately before treatments initiated. Only those wells having a TEER measurement above 200 were included in the experiment. After 16 hour treatments, TEER was measured to determine effects of treatments on TEER. Controls (non-treated cells) were set to 100% as the comparator. Treatment groups are shown as relative percentages compared to the control group TEER. For Lucifer Yellow Permeability experiments, the cells with TEERs above 200 and treated as described in the figure were incubated with Lucifer Yellow (Life Technologies, Grand Island, N.Y. USA) solution for 1 hour at 37° C. The Apical and Basal compartments of the Transwell inserts were sampled and assessed for the presence of Lucifer Yellow. The percentage of Lucifer Yellow which passed through the Caco-2 monolayer was determined by fluorescence measurement of the samples. Data forpercentage of Lucifer Yellow passing the Caco-2 monolayer are presented as fold increase in permeability relative to Controls which were set to a value of 1. A dose-response is demonstrated to *C. difficile* toxin B (Tox B)-mediated cell permeability to the dye, Lucifer Yellow (A) or to electrical resistance of the epithelial layers (TEER, vide supra) (B); in both cases, a non-toxin B control is included (left on graph). The positive neutralizing effect of co-administration of IgM with Toxin B (Tox B) is demonstrated in the Lucifer Yellow permeability study. For the representative permeability in (C), a control sample (no protein, far left bar) shows the permeability of Lucifer Yellow alone, while the remaining bars show the increased permeability by *C. difficile* Toxin B (Tox B), without or without added human serum albumin (HSA), but a neutralizing effect of Toxin B (Tox B) in the presence of IgM (Frac C), second bar from right). For the representative transepithelial electrical resistance measurements (TEER) in (D), a control sample without protein (solid bar, far left) demonstrates the normal electrical resistance of the cell layer, which is considerably reduced in the presence of *C. difficile* Toxin B (Tox B) both without (solid bar, second from left), and with human serum albumin (HSA; solid bar, far right). Restoration of TEER by IgM (Frac. C) in the presence of Toxin B (ToxB) is shown in this figure (Tox B+Frac C; second from right).

As mentioned in the previous example Caco-2 cells are a well characterized model of intestinal epithelia transport and permeability. One of the known consequences of *C. difficile* toxins are intestinal permeability. To test whether purification fractions containing IgM could neutralize this toxin effect, Caco-2 for use as an intestinal permeability model was developed. In this model, Caco-2 cells are differentiated in a monolayer on a well insert with a permeable membrane for 21 days. Following differentiation, permeability can be monitored by measuring the ability of fluorescent small molecules (Lucifer Yellow in this case) to pass through the cell monolayer and by using the TEER method (TransEpithelial Electrical Resistance) to measure the electrical resistance imparted by the monolayer. When the cells have increased permeability, the amount of Lucifer Yellow found on the basolateral side of the membrane is also increased. In terms of electrical resistance, cells with higher permeability have lower resistance. To show that these differences can be measured, a dose response of *C. difficile* Toxin B (FIGS. 3A and 3B) was performed. Both the ability of Lucifer Yellow to across the monolayer and the electrical resistance of the monolayer had appropriate corresponding changes in response to increasing doses of Toxin B. The ability of Fraction C (enriched to 90-95% IgM) to neutralize the Toxin B—mediated permeability was tested. Fraction C and Toxin B were pre-incubated for 1 hr to allow IgM to bind to toxin. Following pre-incubation, cells were treated with the Fraction C and Toxin B mixture for 16 hours. After this 16 hour period cells were assessed for permeability by Lucifer Yellow diffusion across the monolayer (FIG. 3C) and for monolayer TEER (FIG. 3D). For both assay methods, Fraction C provided protection against the Toxin B, whereas HSA had no effect on Toxin B. Lucifer Yellow had a complete reversal while resistance showed only a partial rescue. This is perhaps due to TEER being more sensitive than Lucifer Yellow assay method.

Figure 4A:
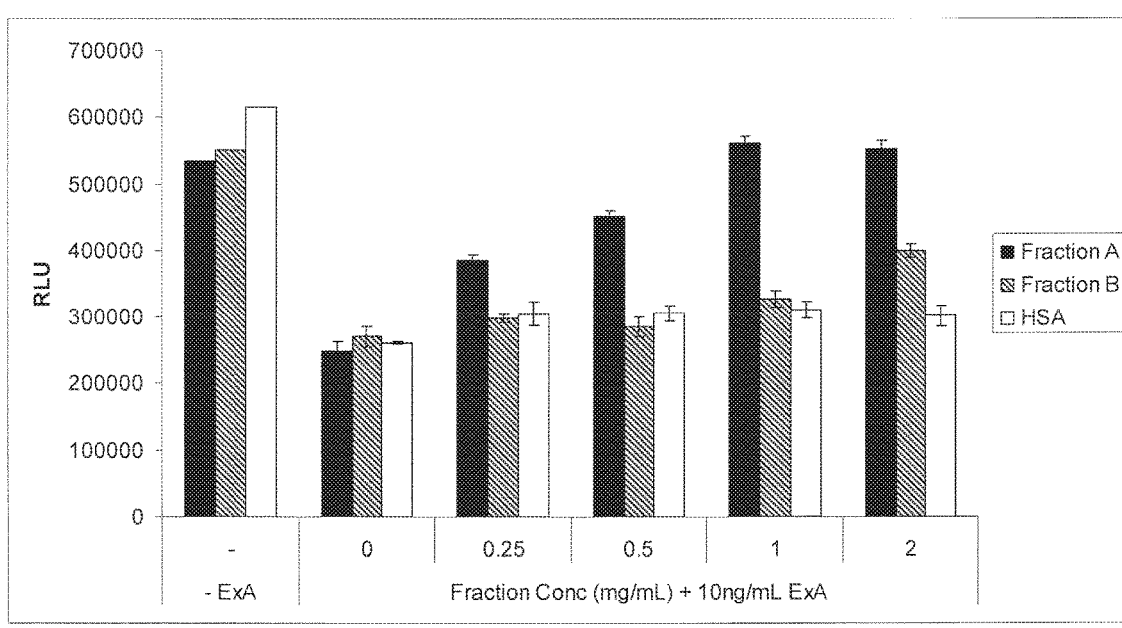
FIGS. 4A and 4B show the neutralization of *Pseudomonas aeruginosa* Exotoxin A cytotoxicity. Caco-2 cells (obtained from ATCC) were cultured in the recommended proliferation media. Cells were seeded in 96-well plates at 4000 cells per well. 24 hours after initial plating, cells were treated with various IgM preparations and/or *Pseudomonas aeruginosa* Exotoxin A as described in the figure legend. Data for the relative number of cells are shown as RLU, as measured by the Cell Titer Glow (Promega Corp. Madison, Wis., USA) assay according to the manufacturer's instructions.
Figure 4B:
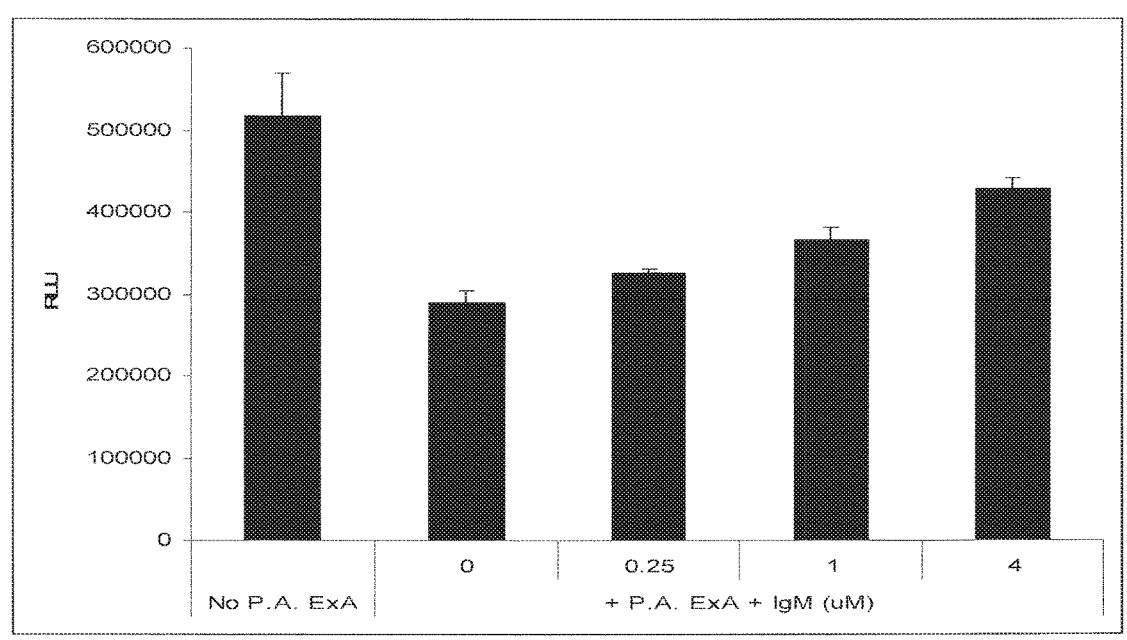

Example 4. Neutralization of Cytotoxic Effects of *Pseudomonas aeruginosa* Exotoxin a Given the positive data from Caco-2 cells with neutralization of *C. difficile* Toxin B, a similar assay in Caco-2 was developed to test *Pseudomonas aeruginosa* Exotoxin A. When Fraction A or Fraction B were assessed in this model, neutralization of Exotoxin A was observed (FIG. 4A). Interestingly, the opposite results were found with Exotoxin A with respect to the efficaciousness of the fractions, compared to *C. difficile* Toxin B; the Fraction A was more potent than Fraction B for neutralization of Exotoxin A. Additionally, we also observed neutralization of *Pseudomonas aeruginosa* Exotoxin A cytotoxicity using purified IgM (FIG. 4B).

Example 5. Neutralization of *Clostridium tetani* Toxoid

Figure 5:
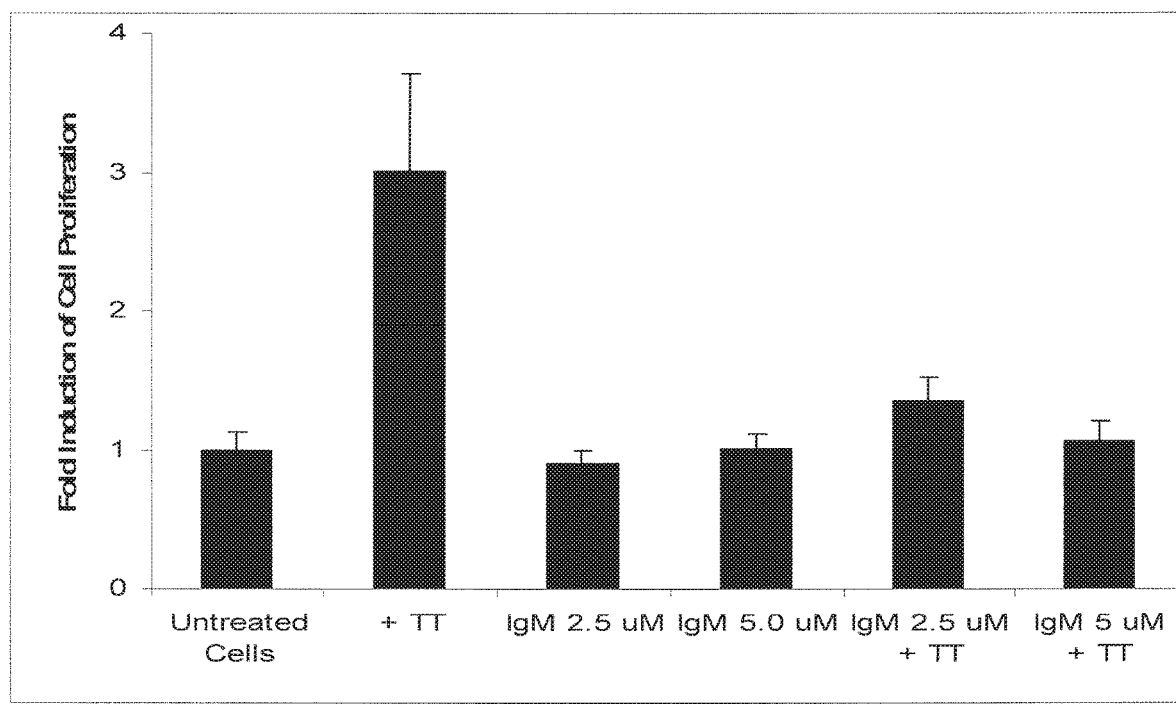
FIG. 5 shows the neutralization of *Clostridium tetani* toxoid effects. Human peripheral blood mononuclear cells were cultured in RPMI with 10% heat inactivated human serum. For proliferation assays, $3 \times 10^5$ cells were seeded in each well of a 96 well plate using culture media. Cells were treated as described in the figure legend. Relative cell proliferation was determined by Cell Titer Glow (Promega Corp. Madison, Wis., USA) and performed according to manufacturer's instructions. Cell proliferation was standardized against experimental controls to a value of 1.

Tetanus toxin is a highly potent neurotoxin that blocks the release of GABA. Most individuals in the United States are vaccinated for tetanus. As a model of tetanus toxin neutralization, a non-toxic toxoid form of tetanus toxin was utilized to assess whether purified IgM can neutralize this protein. It was shown antigenic binding of IgM to the tetanus toxoid (see Table 1). As the toxoid shows no GABA release blockage, IgM's neutralization effect was assessed by proliferation of peripheral blood mononuclear cells (PBMCs). It is known that stimulation of TCR antigens can induce proliferation of T-cells and tetanus is a described stimulant for this proliferation. Therefore, tetanus toxoid induced PBMC proliferation was tested, in the presence and absence of IgM (FIG. 5). A 3-fold increase in cell number in the presence of tetanus toxoid alone was observed, whereas co-treatment with IgM almost completely blocked this effect at 2.5 µM and showed complete inhibition at 5 µM.

Example 6. IgM has Antigenic Recognition of Diverse Microbes

Figure 6:
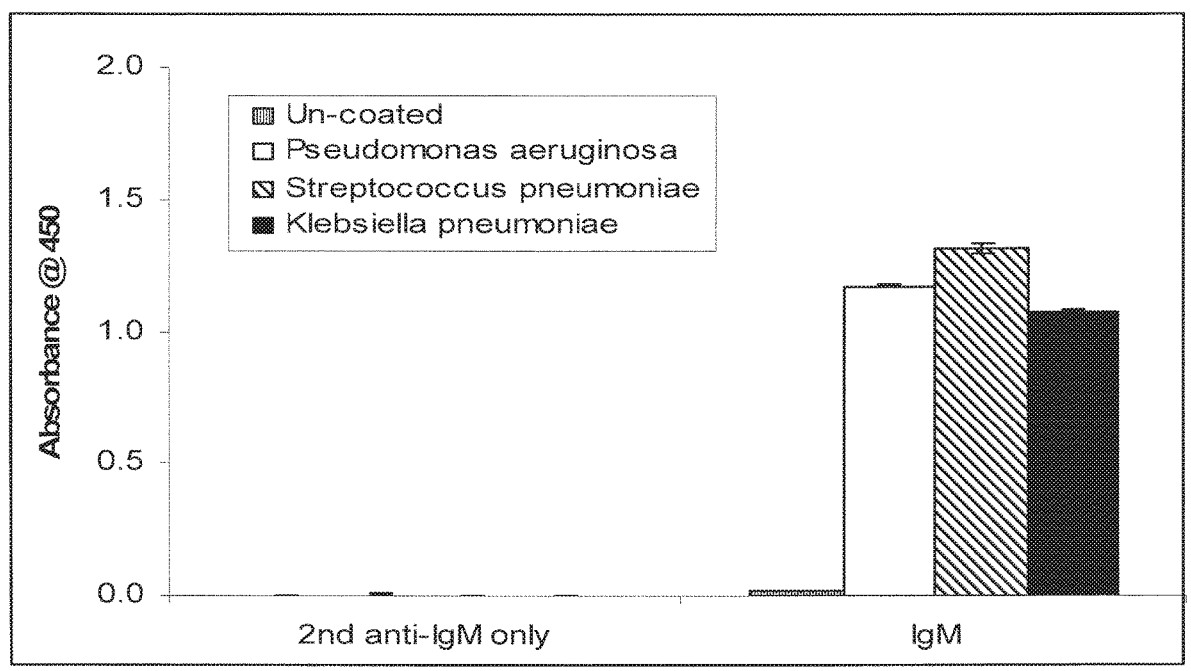
FIG. 6 shows the immunoreactivity of IgM against *Pseudomonas aeruginosa*, *Streptococcus pneumoniae*, and *Klebsiella pneumoniae* bacteria. Absorbance OD readings at 450 nm are shown for representative whole cell ELISAs. Target antigens were formaldehyde treated *Pseudomonas aeruginosa* (white bars), *Streptococcus pneumoniae* (diagonal striped bars), and *Klebsiella pneumoniae* (black bars), whole bacteria cells were coated on ELISA plates. Controls bacteria coated wells incubated with secondary antibody only or wells that have not been coated with antigen.

To better understand the diversity of various targets a variety of ELISAs were performed. A variety of commercially available ELISA kits were used detecting reactivity with both bacterial and viral pathogens. Additionally, an ELISA-based assays was utilized in which whole heat killed or formaldehyde treated microbes were coated on ELISA plates. This assessment allows assessment of reactivity against "global" antigen targets produced by microbes. Data for all ELISAs and Whole Cell ELISAs are summarized in Table 2 and from these data it can be concluded that IgM has ubiquitous antigenic recognition. An example ELISA data set for IgM reactivity in whole cell ELISAs using *Pseudomonas aeruginosa, Streptococcus pneumoniae,* and *Klebsiella pneumoniae* bacteria are shown in FIG. 6.

TABLE 2

Summary of antigenic targets that have been assessed by ELISA and Whole Cell ELISA. The symbol "+" indicates positive IgM reactivity and "+ weak" indicates weak IgM reactivity based on the kit standard controls.

|  | Species | IgM Reactivity |
|---|---|---|
| Viral ELISAs | Adenovirus | + weak |
|  | Cytomegalovirus | + weak |
|  | Measles | + weak |
|  | Mumps | + |
|  | Rubella | + |
|  | Respiratory Syncytial Virus | + |
|  | Varicella-Zoster | + |
|  | Rotavirus | + |
| Bacterial Whole Cell ELISAs | *E. coli* 0111:B4 | + |
|  | *Helicobacter pylori* | + |
|  | *Listeria monocytogenes* | + |

TABLE 2-continued

Summary of antigenic targets that have been assessed by ELISA and Whole Cell ELISA. The symbol "+" indicates positive IgM reactivity and "+ weak" indicates weak IgM reactivity based on the kit standard controls.

| | Species | IgM Reactivity |
|---|---|---|
| | *Legionella pneumophila* | + |
| | *Lactobacillus rhamnosus* | + |
| | *Pseudomonas aeruginosa* | + |
| | *Porphyromonas gingivalis* | + |
| | *Staphylococcus aureus* | + |
| | *Staphylococcus aureus* (Prot. A def.) | + |
| | *Streptococcus pneumoniae* | + |
| | *Clostridium difficile* | + |
| | *Klebsiella pneumoniae* ATCC 10031 | + |
| | *Klebsiella pneumoniae* UNT-127-1 | + |
| | *Pseudomonas aeruginosa* UNT-152-1 | + |
| | *Streptococcus pneumoniae* UNT-011-1 | + |
| Fungal Whole Cell ELISAs | *Candida albicans* | + |

What is claimed is:

1. A method for treating a microbial infection, the method comprising administering to a subject in need thereof a therapeutically effective amount of a composition consisting essentially of a plasma-derived IgM, and, optionally one or more excipients in a diluent or vehicle, wherein:
the plasma-derived IgM is obtained from a waste stream of a standard blood fractionation process; and
the microbial infection is an infection with a microorganism selected from the group consisting of *Aspergillus flavus, Candida albicans, Streptococcus pneumonia, Clostridium difficile, Clostridium tetani, Listeria monocytogenes, Lactobacillus rhamnosus, Escherichia coli, Pseudomonas aeruginosa, Klebsiella pneumoniae, Helicobacter pylori, Legionella pneumophila*, and *Porphyromonas gingivalis*, and
wherein the microbial infection is not an infection with *Staphylococcus aureus*.

2. The method of claim 1, wherein the microbial infection is not an infection with *Clostridium botulinum*.

3. The method of claim 1, wherein the plasma-derived IgM is administered to a subject in a dose of 75 mg to 1 g per kilogram of the subject.

4. The method of claim 1, wherein the plasma-derived IgM is administered to a subject in a dose of 75 mg to 600 mg per kilogram of the subject.

5. The method of claim 1, wherein the plasma-derived IgM is administered to the subject in a dose of 75 mg to 300 mg per kilogram of the subject.

6. The method of claim 1, wherein the plasma-derived IgM is administered daily, every other day, 3 times per week, or once per week.

7. A method for treating a microbial infection, the method comprising administering to a subject in need thereof a therapeutically effective amount of a composition consisting essentially of:
a therapeutic molecule consisting essentially of plasma-derived IgM, and,
optionally one or more excipients in a diluent or vehicle, wherein the microbial infection is an infection with a microorganism selected from the group consisting of *Aspergillus flavus, Candida albicans, Streptococcus pneumoniae, Clostridium difficile, Clostridium botulinum, Clostridium tetani, Listeria monocytogenes*, and *Lactobacillus rhamnosus*; and
wherein the microbial infection is not an infection with *Staphylococcus aureus*.

8. The method of claim 7, wherein:
the microbial infection is a fungal infection; and
the fungal infection is an infection with a fungus selected from the group consisting of *Aspergillus flavus* and *Candida albicans*.

9. The method of claim 7, wherein:
the microbial infection is a bacterial infection; and
the bacterial infection is an infection with bacteria selected from the group consisting of *Streptococcus pneumoniae, Clostridium difficile, Clostridium botulinum, Clostridium tetani, Listeria monocytogenes*, and *Lactobacillus rhamnosus*.

10. The method of claim 7, wherein:
the plasma-derived IgM is obtained from a waste stream of a standard blood fractionation process;
the microbial infection is a bacterial infection;
the bacterial infection is an infection with bacteria selected from the group consisting of *Streptococcus pneumoniae, Clostridium difficile, Clostridium tetani, Listeria monocytogenes*, and *Lactobacillus rhamnosus*; and
the bacterial infection is not an infection with *Staphylococcus aureus*.

11. The method of claim 7, wherein:
the plasma-derived IgM is obtained from a waste stream of a standard blood fractionation process;
the microbial infection is a bacterial infection;
the bacterial infection is an infection with bacteria selected from the group consisting of *Streptococcus pneumoniae, Clostridium difficile, Clostridium botulinum, Clostridium tetani, Listeria monocytogenes*, and *Lactobacillus rhamnosus*; and
the plasma-derived IgM is administered at a dosage sufficient to neutralize cytotoxic exotoxins secreted by the bacteria in the subject.

12. The method of claim 8, wherein the fungus is *Aspergillus flavus*.

13. The method of claim 8, wherein the fungus is *Candida albicans*.

* * * * *